(12) United States Patent
Buglino et al.

(10) Patent No.: US 6,840,924 B2
(45) Date of Patent: Jan. 11, 2005

(54) OSTOMY APPLIANCE

(75) Inventors: Donald Edward Buglino, Titusville, NJ (US); James Donald Jones, Stokesdale, NC (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 10/188,535

(22) Filed: Jul. 3, 2002

(65) Prior Publication Data

US 2004/0006320 A1 Jan. 8, 2004

(51) Int. Cl.$^7$ .................................................. A61F 5/44
(52) U.S. Cl. ...................................... 604/337; 604/344
(58) Field of Search ................................. 604/332–345, 604/355

(56) References Cited

U.S. PATENT DOCUMENTS

| 3,683,918 A | 8/1972 | Pizzella |
| 5,496,296 A * | 3/1996 | Holmberg ................... 604/336 |
| 5,501,678 A * | 3/1996 | Olsen ......................... 604/344 |
| 5,609,585 A * | 3/1997 | Botten et al. ................ 604/332 |
| 5,618,276 A | 4/1997 | Leise et al. |
| 6,332,879 B1 | 12/2001 | Nielsen et al. |
| 6,569,134 B1 * | 5/2003 | Leise et al. ................. 604/332 |

FOREIGN PATENT DOCUMENTS

| EP | 0276042 A | 7/1988 | |
| GB | 2322302 A | 8/1998 | |
| WO | WO 00/53133 | * 9/2000 | ........... A61F/5/443 |

* cited by examiner

*Primary Examiner*—Larry I. Schwartz
*Assistant Examiner*—Linh Truong
(74) *Attorney, Agent, or Firm*—Stuart E. Krieger

(57) ABSTRACT

An ostomy body fitment for attaching an ostomy pouch to a person's body comprises a shapeable adhesive pad, and a shape defining member. In a first annular fixed shape zone, the shapeable pad is supported and shaped by the shape defining member. In a second central reshapeable zone, a portion of the adhesive pad is unsupported by the shape defining member, and can be molded to fit an individual's stoma. A flexible flange for removable adhesive attachment to an ostomy pouch has an attachment zone outside the periphery of the shape defining member, to reduce direct application of external forces.

22 Claims, 10 Drawing Sheets

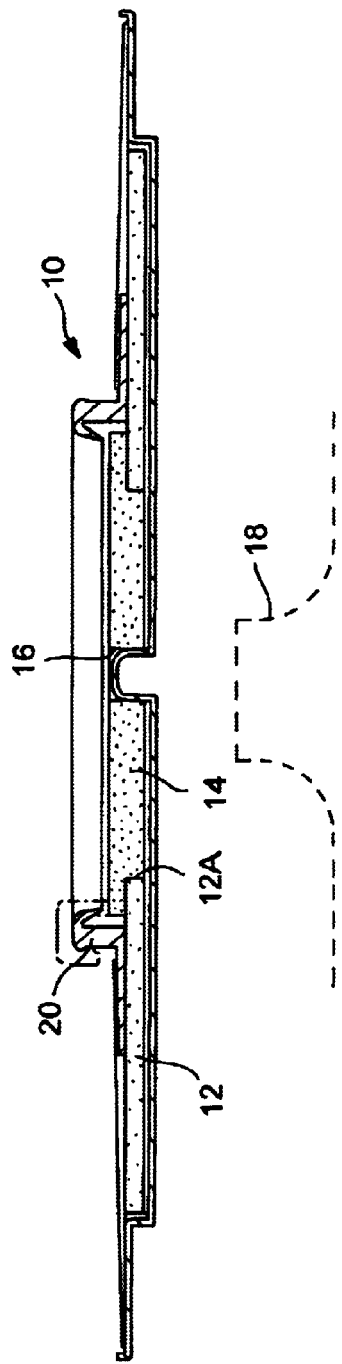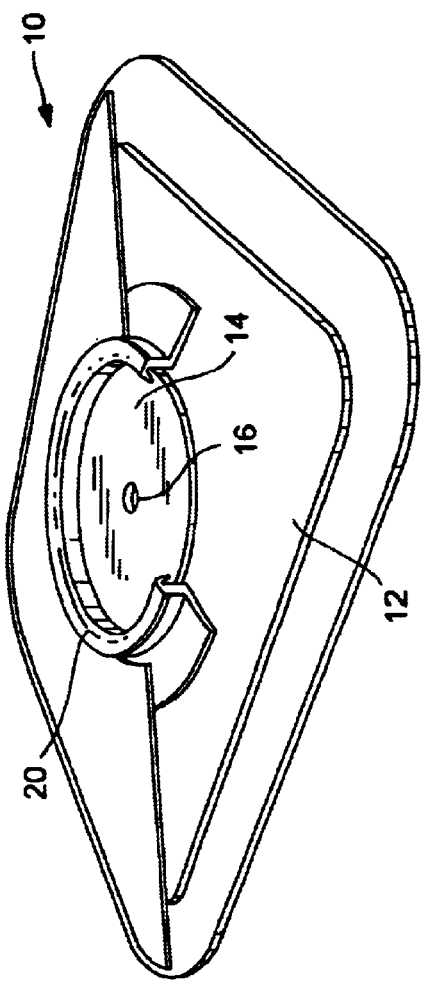
FIG. 1
PRIOR ART
FIG. 2
PRIOR ART ature of the second adhesive 14 means that the second adhesive 14 is capable of any desired shaping, re-shaping, or expansion of the hole 12A formed at the center, in order to fit the size of the stoma 18, and to provide a snug fit around the stoma 18.

It is desirable that the adhesive form a snug fit around the stoma, to prevent faecal matter from soiling the skin around the stoma, which should be kept clean for hygienic reasons.

Reference may also be made to the following additional documents which refer to shapeable adhesives in various forms: U.S. Pat. No. 5,496,296; U.S. Pat. No. 6,312,415; and U.S. Pat. No. 6,332,879. Reference may also be made to WO 00/53133 which describes a convex shaped, pliable adhesive, having an exposable front adhesive surface for attaching to a user's skin, and a non-exposed rear surface which is entirely covered by a backing film.

It would be desirable to yet further improve the versatility of an ostomy appliance using a moldable or shapeable adhesive.

SUMMARY OF THE INVENTION

One aspect of the invention relates to an ostomy body fitment including a pliable adhesive pad. The pad may have a first adhesive surface for contacting a person's skin, and a second adhesive surface opposite the first. A backing overlies and contacts a portion of the second adhesive surface. The combination may define:

a first zone in which the second adhesive surface is substantially exposed at least in use, and a second zone in which the second adhesive surface is contacted by the backing to substantially cover the second adhesive surface.

In the first zone, the exposed adhesive surface may enable the pad to be reshaped manually by folding, or rolling, back a portion of the adhesive pad in the first zone into adhesive contact with a portion of the exposed second adhesive surface. The exposed adhesive surface may thus facilitate or aid pliable shaping the adhesive to a new shape which may be at least partly retained by the adhesive engagement at the exposed second adhesive surface.

The first zone may include a stomal aperture. The exposed second adhesive surface in the first zone may permit enlargement and/or shaping of the aperture by rolling or folding back a rim portion of the adhesive surrounding the aperture, into adhesive contact with a portion of the exposed second adhesive surface.

The term "backing" includes any layer or member in contact with the second adhesive surface. The backing may cause the shape of the adhesive to be more constrained in the second zone than in the first zone. It may also limits reshaping of the adhesive, because the second adhesive surface is not exposed in the second zone.

The backing may be stiff, or it may be flexible. For example, the backing may be a backing film over a portion of the second adhesive surface in the second zone, or it may be a fabric, or it may be some other member, such as a shape defining member for imparting a defined shape to the second zone.

Another aspect of the invention relates to an ostomy body fitment including an adhesive pad having a stomal aperture. At least a region of the pad immediately adjacent to the aperture is shapeable to permit the aperture to be manually enlarged. At least the shapeable region of the adhesive pad comprises a laminate of a first adhesive layer, a second adhesive layer, and a flexible sheet between said first and second adhesive layers.

The term "shapeable" as used herein may refer to a pad or adhesive which might be one or more of the following: stretched, compressed, bent, or at least partly remolded. This contrasts to the majority of adhesive pads which are engineered not to be reshapeable, and instead retain an original shape or configuration of the adhesive.

Preferably, the first adhesive layer provides a first adhesive surface for contacting a person's skin, the second adhesive layer provides a second adhesive surface on an opposite face of the pad to the first adhesive surface, and at least a portion of the second adhesive surface is exposed, at least in use. Preferably the layers are substantially coextensive.

The flexible sheet may provide structural integrity for the adhesive pad. The flexible sheet may limit the amount and/type of (re)shaping which is possible, so that the shapeable region retains a desirable sheet-based form. The flexible sheet may also provide some degree of resilience, to cause the adhesive pad to tighten slightly around a stoma after shaping, in order to ensure a snug fit around the stoma.

Another aspect of the invention relates to an ostomy body fitment including an adhesive pad having a compliant or shapeable property allowing the pad to be shaped. A shape defining member on one side of the pad has a contour to impart a bulged, or convex, shape to the adhesive pad. The combination of the adhesive pad and the shape defining member defines:

a first fixed-shape zone in which the adhesive is supported by, and has a shape defined by, the shape defining member; and a second shapeable zone in the which the adhesive pad is unsupported by the shape defining member, and is shapeable to enable the pad and an aperture therein to be custom shaped to fit an individual's stoma.

This aspect of the invention therefore allows the same adhesive pad to provide both a region of well defined shape for secure attachment to the skin, and a shapeable region for enabling a custom fit to be molded for an individual's stoma. This removes the need to provide different adhesives, or different adhesive consistencies, or different adhesive thicknesses to provide the different adhesive characteristics in different zones.

The invention may also provide a practical way in which a pressure applying surface (pressure ring) can be used with a shapeable adhesive, for applying pressure to protrude a recessed stoma.

Another broad aspect of the invention provides a one-piece ostomy pouch including a region of shapeable adhesive around a stomal aperture. The shapeable adhesive permits the stomal aperture to be enlarged and/or custom shaped from outside the rear (body facing side) of the pouch, by pliably shaping the aperture in the shapeable adhesive.

Hitherto, it is unknown to provide such a shapeable adhesive with a one-piece pouch. Conventionally, shapeable adhesives are known only with two-piece appliances. This is principally because the conventional approach is to access the shapeable adhesive from the bag-facing side of the body-fitment, and to mold the adhesive to the desired shape and form only from the bag-facing side.

A further broad aspect of the invention relates to a body fitment for removable attachment to an ostomy pouch, and including a pliable adhesive pad. A shape defining member on one side of the adhesive pad imparts a predetermined shape to a portion of the adhesive pad leaving a second portion unsupported and pliably reshapeable. The body fitment also includes a flange for permitting adhesive attachment of an ostomy pouch to the flange. The flange may be flexible, and a peripheral portion of the flange is unsecured.

This can provide a body fitment using a shapeable adhesive, which can at least partly isolate the shape defining member (which applies forces to the body) from a peripheral region of the flange to which load bearing forces may be applied. Such forces may be applied either when the pouch is pressed against the flange during attachment of the pouch, or when the pouch is worn in use and is supported by the body fitment.

In one form, it is preferred that an attachment zone or "landing zone" on the flange have an inner periphery which lies outside the outer periphery of the shape defining member.

In another form, it is preferred that a complementary (second) flange on the pouch, for adhesive attachment to the first (first-mentioned) flange, has an inner periphery which is larger than at least one of the inner and outer peripheries of the shape defining member. This may isolate the shape defining member from external forces. The geometry of the flanges may also provide a significant degree of flexibility of the flanges even when a relatively rigid shape-defining member is used.

A further broad aspect of the invention extends the principle of the above geometry to body fitments which might not include a pliably shapeable adhesive, but which still benefit from isolation of external forces from a pressure applying member of the body fitment. More specifically the fourth broad aspect of the invention relates to a body fitment for removable attachment to an ostomy pouch, and including a pressure ring for applying pressure to the skin around a stoma, to encourage protrusion of a recessed stoma. The body fitment also includes a flange for permitting adhesive attachment of an ostomy pouch to the flange. The flange may be flexible, and a peripheral portion of the flange is unsecured.

In a similar manner to the previous aspect described above, this can provide a body fitment which can at least partly isolate the pressure ring (which applies forces to the body) from a peripheral region of the flange to which load bearing forces may be applied. Such forces may be applied either when the pouch is pressed against the flange during attachment of the pouch, or when the pouch is worn in use and is supported by the body fitment.

In one form, it is preferred that an attachment zone or "landing zone" on the flange have an inner periphery which lies outside at least one of the inner and the outer peripheries of the pressure ring.

In another form, it is preferred that a complementary (second) flange on the pouch, for adhesive attachment to the first (first-mentioned) flange, has an inner periphery which is larger than at least one of the inner and outer peripheries of the pressure ring.

Although the above aspects of the invention have been described separately, it will be appreciated that yet further advantages may be obtained by combining together two or more of the above aspects.

Although certain selected features have been highlighted above, the invention is not limited only to these selected features. Further features, advantages and objects of the invention will become apparent from the appended claims and drawings, and from the following non-limiting description of preferred embodiments of the invention. The Applicant claims protection for any novel feature or combination of features described herein and/or illustrated in the drawings, whether or not emphasis has been placed thereon.

BRIEF DESCRIPTION OF THE DRAWINGS

Non limiting embodiments of the invention are now described, by way of example, with reference to the accompanying drawings, in which:

FIG. 1 is a schematic section through a conventional body-side member, as disclosed in GB-A-2290974;

FIG. 2 is a partially cutaway perspective view of the body-side member of FIG. 1;

DETAILED DESCRIPTION OF PREFERRED EMBODIMENTS

Referring to FIGS. 3–6, a first embodiment of the invention is illustrated in the form of a one-piece pouch 30. This application of a shapeable adhesive with a one-piece pouch is believed to be novel in one non-limiting aspect of the invention.

The pouch 30 comprises front and rear walls, 32 and 34 respectively, welded together around their periphery 36 to define a pouch envelope. The walls 32 and 34 are of a liquid and gas impermeable material, for example, a laminate of one or more layers of polyvinylethylene (PVE) and a barrier layer of polyvinyledine chloride (PVDC). A comfort layer 38 of a soft, cushioning material may be provided outside the front and rear walls 32 and 34, and secured in the weld at the periphery 36. Although not shown explicitly, the pouch 30 may be provided with a conventional filtered vent for allowing gases to vent through a deodorizing filter. The bottom of the pouch 30 may be closed, or it may be provided with a closable, drainage chute for allowing the pouch contents to be drained.

Figure 5:
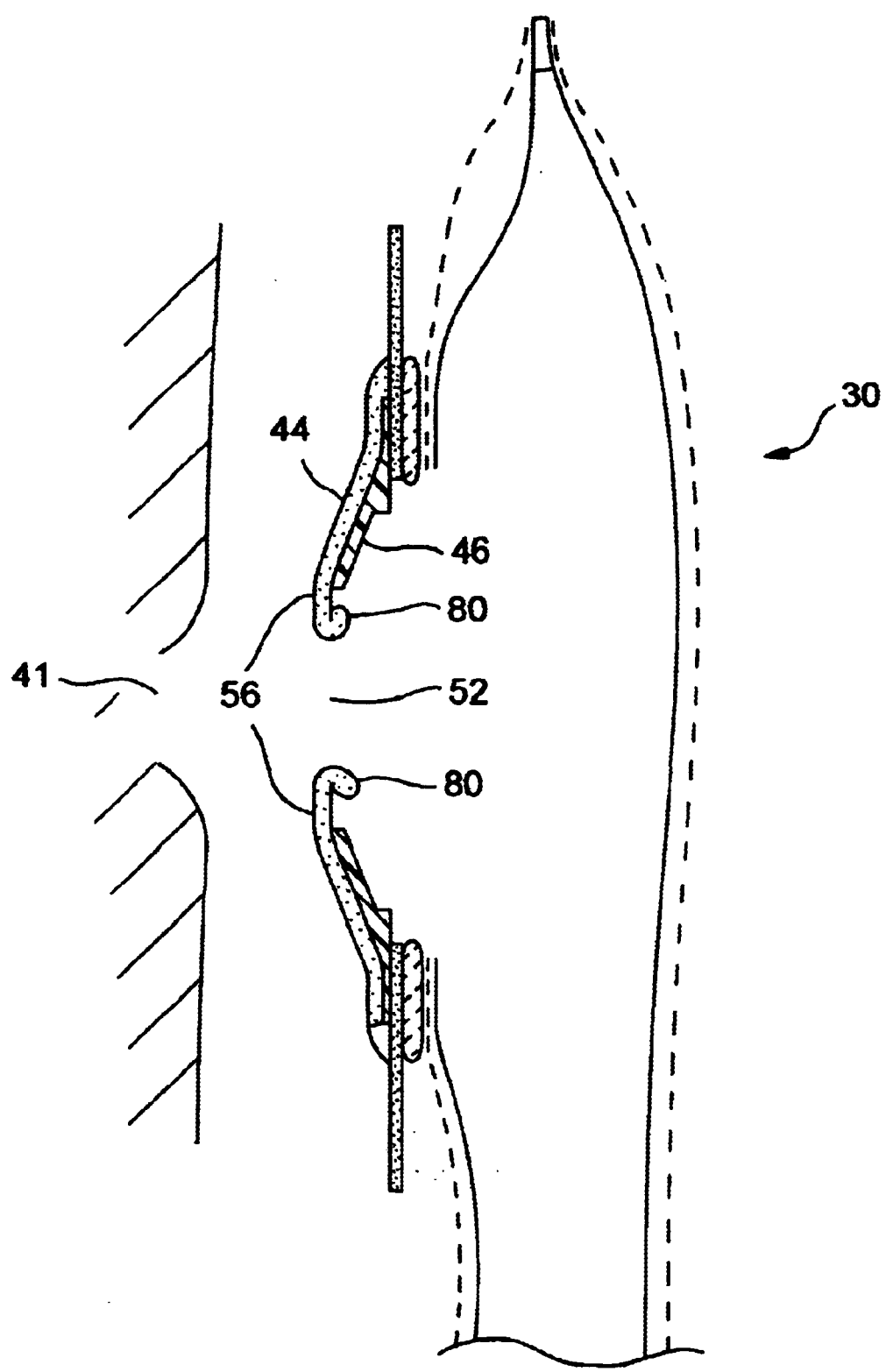
FIG. 5 is a schematic section showing how the pouch of FIG. 3 is prepared for use.
Figure 6:
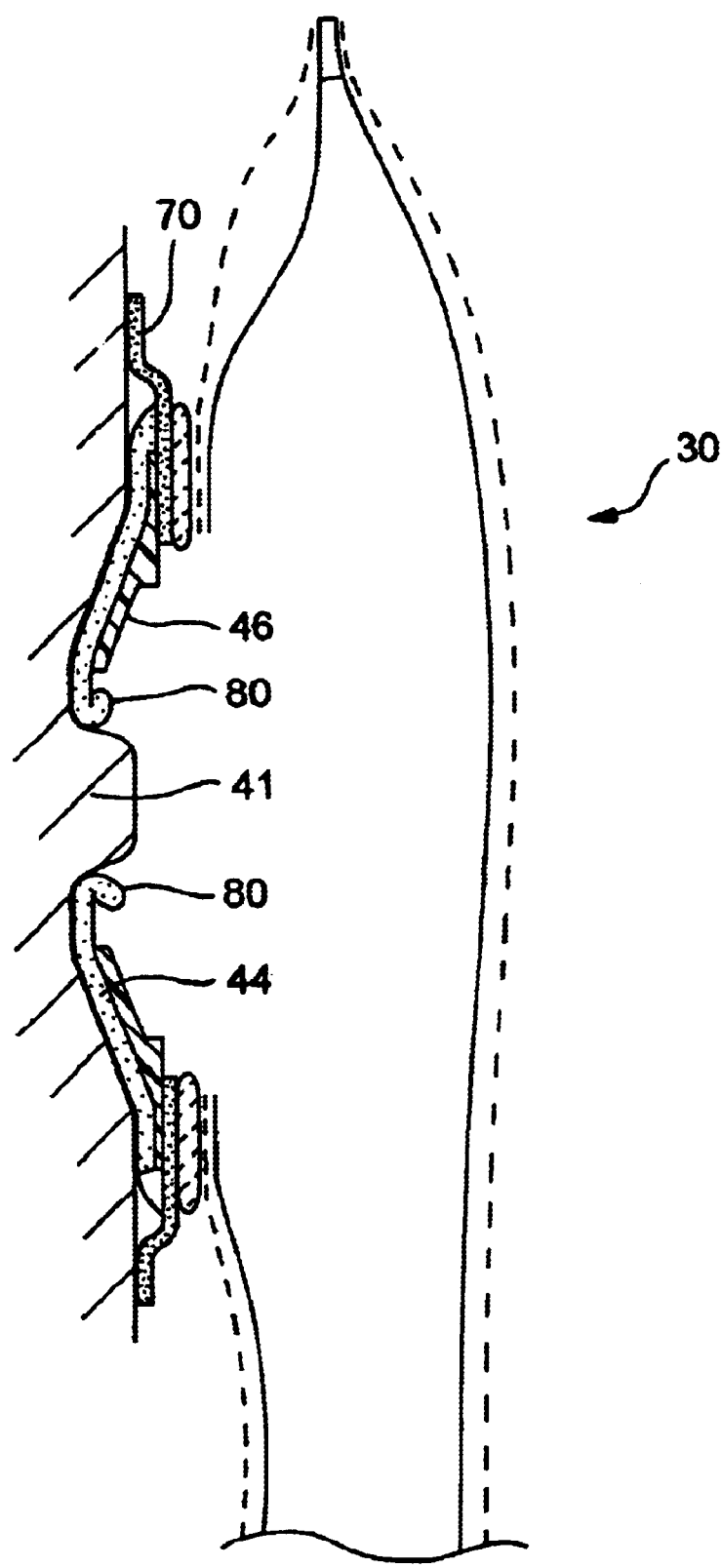
FIG. 6 is a schematic section showing the pouch of FIG. 3 in a fitted condition.

The rear wall 34 includes a stomal aperture 40 for receiving body waste from a wearer's stoma 41 (FIGS. 5 and 6). An adhesive body fitment 42 is secured to the rear wall 34 around the stomal aperture 40 for adhesively fastening the pouch 30 to a peristomal region of the body.

The fitment 42 comprises a pad 44 of a pliable and/or moldable and/or shapeable body adhesive, mounted around a shape defining member 46. The shape defining member 46 is of a resiliently flexible, but relatively stiff, plastics. The shape defining member 46 can therefore be flexed in use during fitting and wearing of the pouch 30, but returns towards its natural shape to support the adhesive pad 44, and to apply pressure to the skin. In this embodiment, the shape defining member 46 is shaped to define a bulge towards the stoma, for applying pressure to the skin around the stoma, to encourage protrusion of the stoma. The body defining member generally includes a base 48 from which extends a convex-shaped wall 50. In a region adjacent to the base 48, the plastics may have a greater thickness, providing increased stiffness in this region.

The adhesive pad 44 and the shape defining member 46 are both of a generally closed loop shape, in this embodiment circular or annular. The diameter of the central aperture 52 in the adhesive pad 44 (pad aperture) is smaller than the diameter of the central aperture 54 in the shape defining member 46 (member aperture), such that a region 56 of the adhesive 44 extends generally unsupported in the open center of the shape defining member 46.

The pad aperture 52 may generally be between about 5 mm and 60 mm in diameter, or preferably between about 10 mm and 55 mm, more preferably between about 12 mm and 50 mm. In one form, the pad aperture is generally about 12–14 mm in diameter.

Preferably, although not essentially, the diameter of the pad aperture 52 may be less than about two thirds of the diameter of the member aperture 54, more preferably less than about half, more preferably less than about one third. The width of the adhesive from an edge of the member aperture 46 to a closest edge of the pad aperture 52 may be at least 3 mm, more preferably at least 5 mm, more preferably at least 7 mm.

The combination of the shapeable adhesive 44 and the shape defining member 46 therefore defines a first zone 60 and a second zone 58. In the second zone 58, the adhesive 44 has a well defined shape (defined by the underlying shape defining member 46). In the first zone 60, the adhesive 44 can be pliably shaped by the ostomate to create a central aperture 52 of any desired size and shape, and to create a customized shape or profile in the adhesive to fit snugly around his or her stoma.

In this embodiment, the adhesive pad 44 has a substantially uniform thickness from one edge to an opposite edge, through both the first and second zones 60 and 58. In other words, this design removes the need for the adhesive thickness in the second zone 58 to be reduced in order to provide a different material characteristic from the first zone 60. This difference in characteristic is provided instead by the underlying shape defining member 46 in the second zone 58. Also in this embodiment, the adhesive pad 44 has a substantially uniform consistency, being the same in both the first and second zones 58 and 60. In other words, this design removes the need to use different adhesive consistencies for the first and second zones 58 and 60 to provide different material characteristics. This difference in characteristic is provided instead by the underlying shape defining member 46 in the second zone 58. These features provide important advantages in terms of cost and ease of manufacture.

Figure 3:
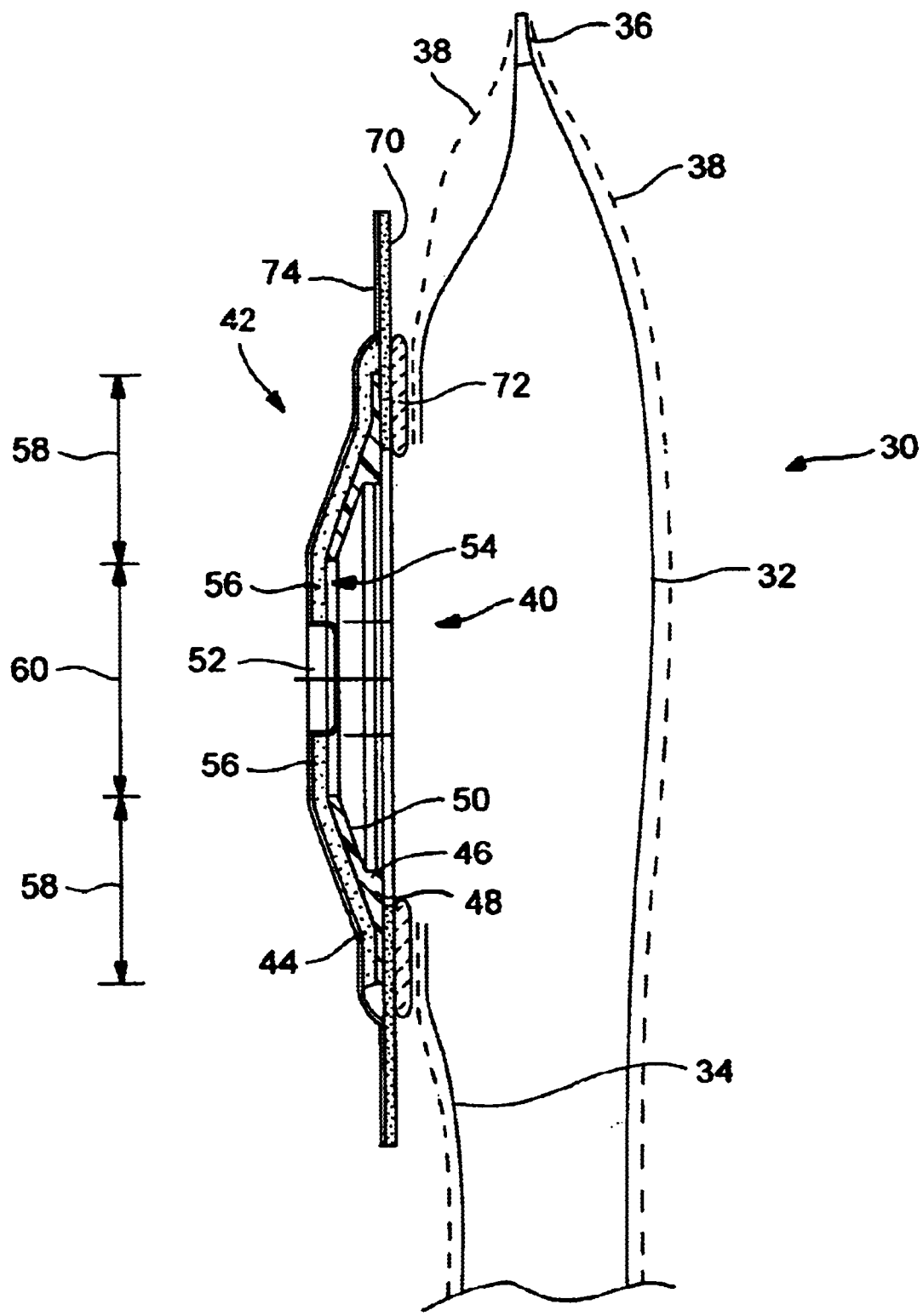
FIG. 3 is a schematic section through the body-attachment region of an ostomy pouch according to a first embodiment of the invention.
Figure 4:
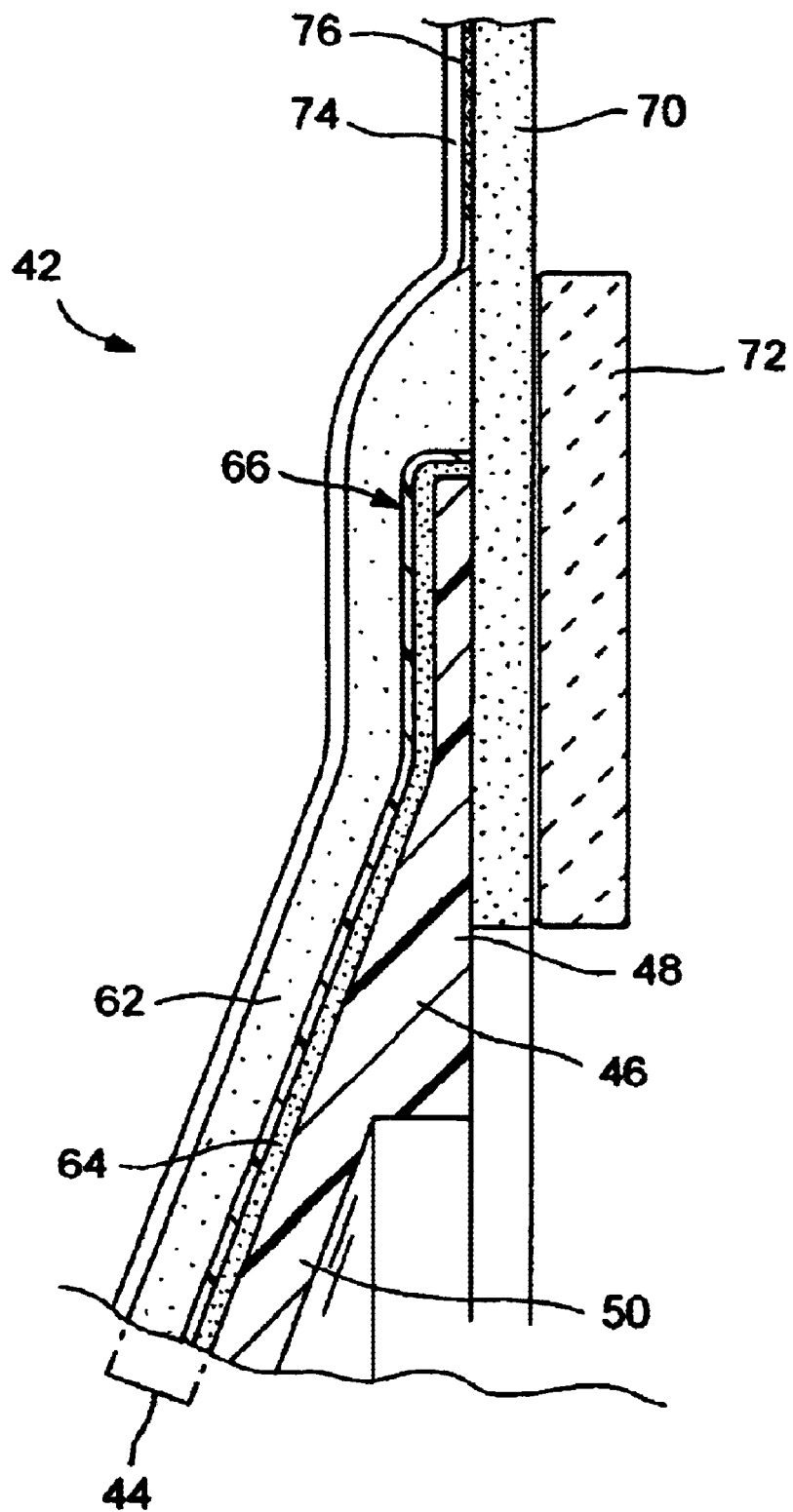
FIG. 4 is an enlarged section showing a detail of the body fitment from FIG. 3 in isolation.

As best seen in FIG. 4, the adhesive pad 44 comprises a laminate of a first adhesive layer 62 and a second adhesive layer 64 sandwiching a layer 66 of a flexible plastics, for example, polyethylene. The pad 44 is shapeable, in that the pliable nature of the adhesive layers 62 and 64 and of the plastics 66 permits the pad to be substantially folded or rolled from an edge. The first adhesive layer 62 provides a first adhesive surface for contacting the wearer's skin (see FIG. 6), and the second adhesive layer 64 provides a second adhesive surface opposite the first adhesive surface. In the second zone 58, the shape defining member 46 contacts and substantially covers the second adhesive surface, so that the second adhesive surface is substantially non-exposed. Radially outwardly of the second zone 58 (defined by the shape defining member 46), the second adhesive surface may also be contacted and substantially covered by a flexible microporous adhesive patch 70. In the first zone 60, the second adhesive surface (i.e. facing away from the body and towards the interior of the pouch) is substantially exposed. This exposed adhesive surface permits the pad aperture 52 to be re-shaped or enlarged by rolling and/or folding back a rim portion 80 of the pad around the pad aperture 52, into adhesive contact with a portion of the second adhesive surface of the pad 44 facing away from the body. The adhesive contact may at least partly secure the re-shaped rim 80 in its new shape, or at least partly balance internal forces in the adhesive pad 44, so that the rim 80 can retain its new shape, at least temporarily during the fitting of the body fitment 42 to the peristomal area of the body. The layer 66 of flexible plastics in the laminate of the adhesive pad 46 may be embossed and may serve to provide structural integrity for the pad 44, and also to maintain the pad in a sheet-based form, even after reshaping of the rim 80. The layer 66 may also be at least partly resilient, and may tend to cause the adhesive pad 44 to tighten slightly around a stoma after re-shaping, in order to ensure a snug fit around the stoma.

In each layer 62, 64, the adhesive may be generally not transferable from one zone 58, 60 to another. For example, the adhesive in each layer is generally not transferable from the second zone 58 to the first zone 60. It may be seen that the first adhesive layer 62, that provides the skin-contacting adhesive surface, extends across both the first and second zones 60 and 58.

Many different types of medical grade adhesive may be used for the first and second adhesive layers 62 and 64. In the present embodiment, a hypoallergenic hydrocolloid based adhesive is preferred, such as that produced by ConvaTec under the name Durahesive. Such an adhesive is generally tacky, putty-like, and substantially non-elastic, with low memory.

The first adhesive layer 62 may be thicker than the second adhesive layer 64. The first adhesive layer 62 may have a thickness of between about 1 mm and 1.5 mm, typically about 1.27 mm. The second adhesive layer may have a thickness of between about 0.2 mm and 1 mm, typically about 0.5 mm.

The microporous adhesive fabric patch 70 extends radially outside the body adhesive 44. The body fitment 42 also includes a conventional belt attachment ring 72 having horizontally disposed belt attachment lugs (not visible in the drawings) for allowing additional support for the pouch from a belt (not shown). In this embodiment, the belt attachment ring 72 is formed separately from the shape defining member 46, and the two are secured as part of a unitary assembly using, for example, plastics welding. However, if desired, the belt attachment ring 72 and the shape defining member 46 may instead be integrally molded.

The body-facing surface (first adhesive surface) of the adhesive pad 44 and of the fabric patch 70 are initially covered with suitable cover sheets 74 and 76, which may be of, or coated with, a suitable material (e.g. silicon) to aid release from the adhesive surfaces. The cover sheet for the adhesive pad 44 is preferably contoured to match the shape of the adhesive 44 and may, advantageously, include a central depression for locating in the central aperture 52 of the adhesive 44. Although not shown, the second adhesive surface of the adhesive pad 44 may, in the first zone 60, also be protected by a removable release sheet intended to be removed to expose the second adhesive surface when in use.

Referring to FIG. 5, to fit the pouch 30, the user first removes the protective cover sheet (74 not shown in FIG. 5) from the adhesive pad 44. Using, for example, a finger, the user then shapes the region 56 of the adhesive in the central aperture of the shape defining member 46, to match his or her shape and size of stoma 41. Typically, the central aperture 52 will need to be enlarged. Since the user only accesses the adhesive from one side (i.e. from the left in FIGS. 3 and 5), the user will typically enlarge the aperture 52 by rolling or folding back the rim 80 of the aperture inwardly, into adhesive contact with the exposed second adhesive surface of the pad 44. This may form a rolled or folded lip.

Referring to FIG. 6, the body fitment 42 is then pressed against the peristomal area of the body. The shape defining member 46 applies pressure to the skin to tend to protrude a recessed stoma 41, so that the exudate can be directed into the pouch. The custom shaped portion (rim 80) of the adhesive 44 forms a custom fit around the stoma 41, shaped by the user according to the user's experience and preferences.

Portions of the cover layer (76 not shown in FIG. 6) can then be peeled from the fabric patch 70, and the patch 70 can be smoothly adhered to the skin around the body adhesive 44.

Figure 7:
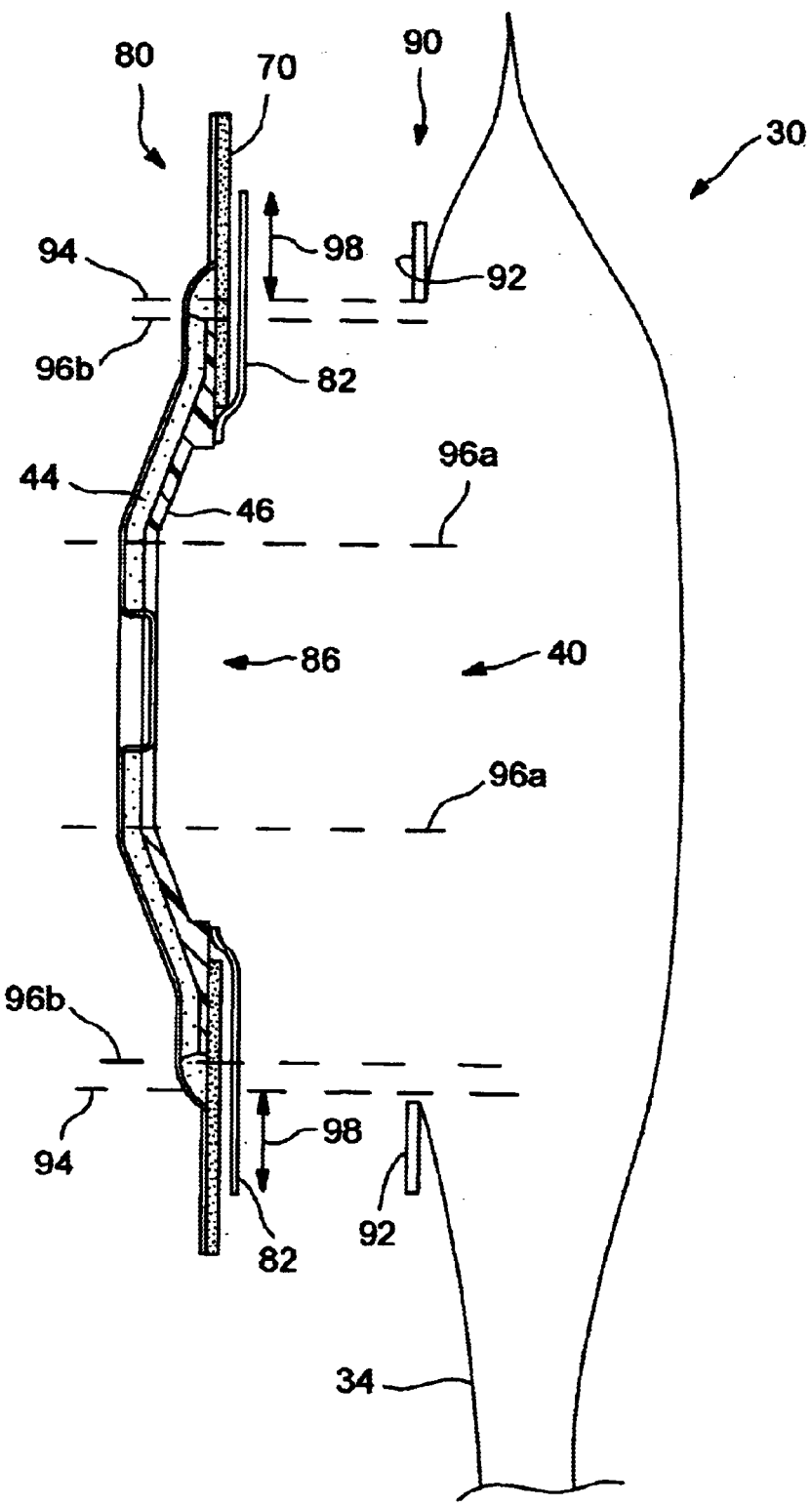
FIG. 7 is a schematic section through the body-fitment region of a second embodiment of the invention.
Figure 8:
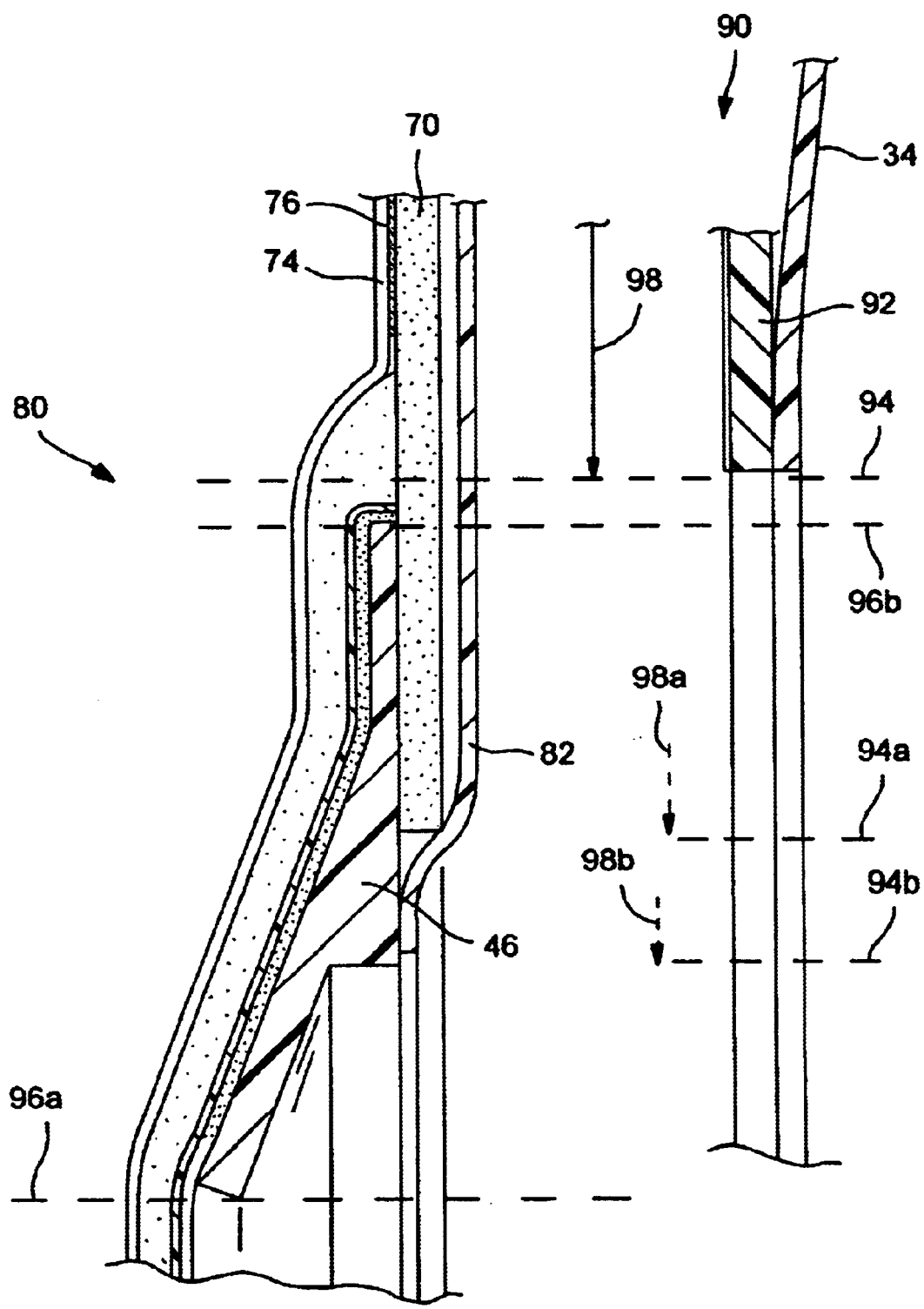
FIG. 8 is an enlarged section showing a detail of FIG. 7.

Referring to FIGS. 7 and 8, a second embodiment of the invention is shown in the form of a two-piece ostomy appliance. This shares similar features with the first embodiment, and equivalent features are, where appropriate, denoted by the same reference numeral.

The main difference between the first and second embodiments is that, in the second embodiment, the body fitment 80 is not permanently secured to the pouch 30, but is a separate unit removably attachable to the pouch 30. The body fitment 80 consists of the body adhesive pad 44, the shape defining member 46 and the fabric patch 70 previously described. Additionally, the body fitment includes a coupling portion (82) for coupling to the pouch 30. In this embodiment, the coupling portion is in the form of a flange 82 to which the pouch 30 is adhesively attachable. The flange 82 may be of a material which may be generally flexible, and may be at least partly resilient to deformation out of its normal plane. The flange may be generally non-stretchable in the plane, or it may be resiliently stretchable. A suitable material for the flange is, for example, polyethylene.

The flange 82 is secured to the fitment around the stomal aperture 86, such that at least the outer periphery of the flange 82 is unattached, and provides a degree of free movement relative to the adhesive pad 44 and to the shape defining member 46. It may be seen that first layer 62 of adhesive providing the skin contacting adhesive surface extends generally in both the first and second zones 60 and 58.

The pouch 30 comprises a complementary coupling portion 90 in the form of a bag-side, adhesive-bearing flange 92. The adhesive may be a so-called peelable resealable adhesive known in the art for allowing the adhesive to be removed and re-attached at least a plurality of times while still providing a reliable adhesive attachment. In this embodiment, the flange 92 may be flexible, and may be at least partially resilient to deformation out of its normal flat plane. The flange 92 may be resistant to stretching within the plane, or it may be resiliently stretchable. The flange 92 is secured to the rear wall 34 of the pouch 30 around the stomal aperture 40, such that at least a peripheral portion of the flange 92 is unattached, and provides a degree of free movement relative to the pouch wall 34 (in a similar manner to the flange 82 described above). A suitable material for the adhesive-bearing flange is a closed cell polyethylene foam, and the adhesive may be a hypoallergenic pressure-sensitive acrylate adhesive.

Such an arrangement including flexible flanges 82 and 92 may provide a desirable amount of flexibility in the coupling between the pouch and the body fitment, even though the body-fitment includes a relatively rigid shape defining member, or pressure applying member, 46.

As best seen in FIG. 8, the inner diameter of the aperture in the bag-side flange 92 (delimited by lines 94) may be larger than the inner diameter of the shape defining member 46 (delimited by lines 96a). The inner diameter of the aperture in the bag-side flange 92 may also be larger than the outer diameter of the shape-defining member 46 (delimited by lines 96b). Although not essential, in the latter case (illustrated in FIG. 8), when the bag-side flange 92 is pressed against the flange 82, the inner periphery of the bag-side flange 92 lies radially or transversely outside the outer periphery of the shape defining member 46. Thus, the bag-side flange 92 surrounds the shape defining member 46, but does not directly overlap, or directly overlie, any portion of the shape defining member 46. This may be advantageous in preventing compression forces from being applied directly to the shape defining member 46 (which applies pressure to the skin) when the flanges 92 and 82 are pressed together to attach the pouch to the body fitment 80. Instead the flexibility of the flanges 82 and 92 permits the flanges to be pressed against each other without undue pressure on the shape defining member 46. Also, after attachment of the pouch, while the pouch is being worn, the above geometry of the bag-side flange 92 relative to the shape defining member 46 can de-couple direct axial forces between the shape-defining member 46 (which applies pressure to the skin), and the pouch 30. Instead, such forces are applied through the flexible flanges, which provides a degree of shock absorption. Also, during removal of the pouch, the separation forces applied to the flanges 82 and 92 are somewhat decoupled from the shape defining member 46.

In an alternative form, the inner diameter of the aperture in the bag-side flange 92 (delimited by lines 94) may lie between the inner and outer diameters of the shape defining member 46 (delimited by lines 96a and 96b). The bag-side flange 92 may be dimensioned such that, when the bag-side flange 92 is pressed against the flange 82, the inner periphery of the bag-side flange 92 may at least partly overlap or partly overlie the shape defining member 46. In one form, the bag-side flange but does not substantially overlap or overlie at least a majority of the area of the convex-shaped wall 50. For example, the aperture in the bag-side flange may be dimensioned as indicated at 94a or 94b. In a similar manner that that described above, such a geometry, in combination with the flexible flanges 82 and 92, may substantially decouple the shape defining member 46, and in particular the convex portion 50, from direct exposure to external forces during attachment, use and disconnecting of the pouch relative to the body fitment.

The difference between the inner diameter of the bag-side flange 92 and at least one of the inner and outer diameters of the shape defining member 46 may be less than about 20 mm, more preferably less than about 10 mm, and more preferably less than about 5 mm.

The portion of the flange 82 to which the bag-side flange 92 attaches is an attachment zone or "landing zone" 98, lying radially or transversely outwardly of at least one of the inner and outer peripheries of the shape defining member 46. Such a landing zone may be defined explicitly. The position of the landing zone 98 may depend on the size of the aperture in the bag-side flange 92 (delimited by lines 94). For example, the landing zone may extend to a position 98a or 98b, to match a particular diameter of the aperture in the bag-side flange 92 (delimited by lines 94a and 94b). Alternatively, the flange 82 may be substantially plain, but larger than the bag-side flange 92 to enable the user to center the bag-side flange 92 on the flange 82 by feeling the relative alignment of the flanges. If desired, a lip (not shown) may also be provided upstanding from the inner or outer periphery one flange, to align the flanges 82 and 92.

Although the second embodiment uses the same shapeable adhesive pad 44 as that described for the first embodiment, it will be appreciated that the same geometric relationship between the flanges 82 and 92, and the relatively stiff pressure ring 46, may be used in other embodiments with a conventional, non-shapeable adhesive. The geometric relationship can reduce the exposure of the pressure ring to external forces, either when fitting the pouch, or when the pouch is worn.

Figure 9:
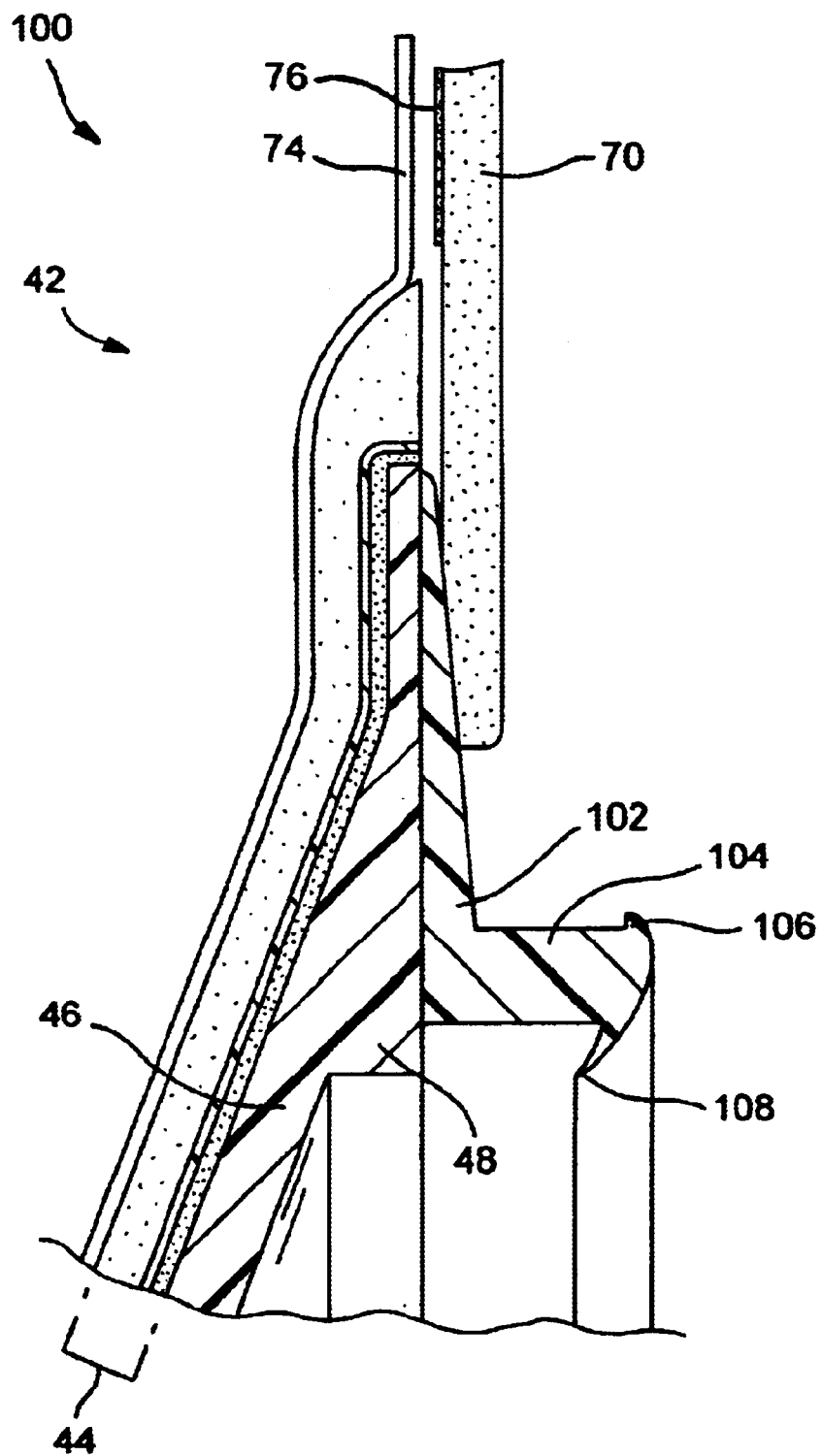
FIG. 9 is a schematic section showing a body-fitment of a third embodiment of the invention.

FIG. 9 shows an alternative third embodiment in the form of a two-piece ostomy appliance. This embodiment is similar to the second embodiment, and the same reference numerals are used where appropriate.

The principal difference in the third embodiment is that a mechanical fastening arrangement is used for releasably coupling the pouch to the body fitment 100, instead of an adhesive fastening arrangement as in the second embodiment.

Referring to FIG. 9, the body fitment 100 includes the adhesive pad 44, the shape defining member 46 and the patch 70 described previously. In addition, a molded plastics coupling ring 102 is secured to the base 48 of the shape defining member 46, for coupling to a bag-side coupling ring (not shown) in a similar manner to that depicted in FIG. 1. Many different mechanical couplings are known in the art for forming such a releasable connection between a body fitment and a pouch. In the present embodiment, the coupling ring 102 comprises an upstanding rib 104 having an outwardly facing locking projection 106 for mechanical engagement with a complementary formation on the bag side coupling ring (not shown). The rib 104 also carries a deflectable seal fin 108 for sealing against the bag-side coupling ring.

In the present embodiment, it is preferred that the shape defining member 46 and the coupling ring 102 be molded separately, and then secured together directly or indirectly. This simplifies molding of the desired shapes, which might otherwise be difficult to mold in a single mold. However, in other embodiments, it may be preferred to integrally mold the shape defining member 46 and the coupling ring 102 as a one-piece item.

Figure 10:
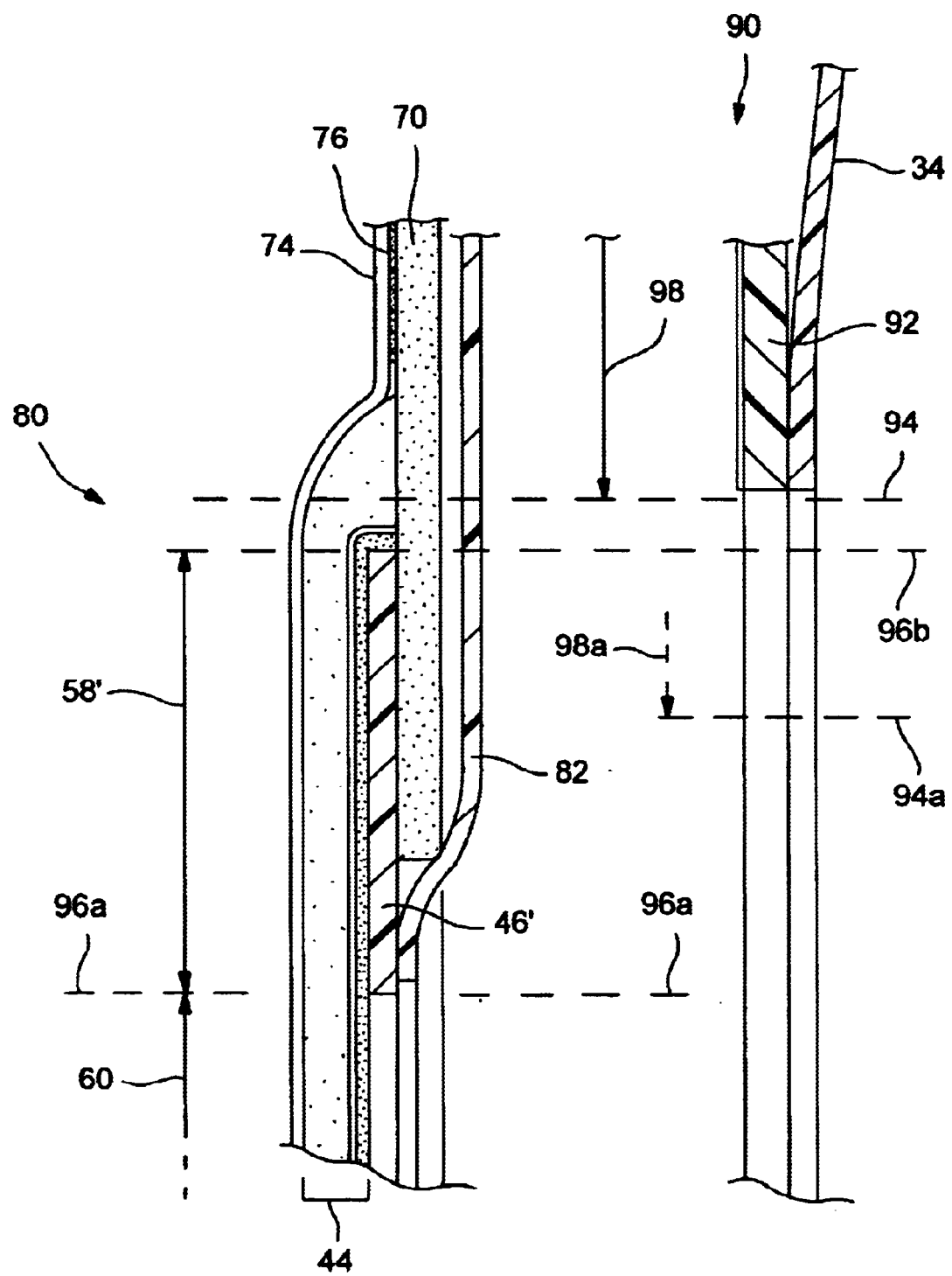
FIG. 10 is a schematic section showing a body-fitment of a fourth embodiment of the invention.

FIG. 10 shows an alternative fourth embodiment based on the principles of the second embodiment. Equivalent reference numerals are used where appropriate.

The principal difference in the fourth embodiment is that the convex shape defining member (46) is replaced by a generally planar shape defining member 46' in the form of a generally flat ring or washer. The shape defining member 46' and the adhesive pad 44 combine to define the first zone 60 in which the adhesive pad 44 is generally unsupported and is shapeable to fit an individual's stoma, and the second zone 58' in which the adhesive has a well-defined shape, in this case a generally planar shape. In this embodiment, the geometry between the inner periphery of the landing zone 98 and the outer periphery of the shape-defining member 46' is maintained as in the second embodiment, to at least partly decouple the shape-defining member 46' from external forces through the flange 82. In particular, the inner periphery of the bag-side flange 92 (delimited by lines 94) may be dimensioned to lie radially outwardly of the inner periphery of the shape defining member. In the embodiment illustrated in FIG. 10, the inner periphery of the bag-side flange 92 may also be dimensioned to lie radially outwardly of the outer periphery of the shape defining member (delimited by lines 96b). Alternatively, the inner periphery of the bag-side flange 92 may lie generally between the inner and outer peripheries of the shape defining member 46', for example, as indicated at 94a.

Also, in the illustrated embodiment, the exposed second surface of the adhesive pad 44 (facing away from the body side surface of the adhesive pad) is present in the first zone 60, as in the previous embodiments, to facilitate pliable reshaping of the pad aperture 52.

Figure 11:
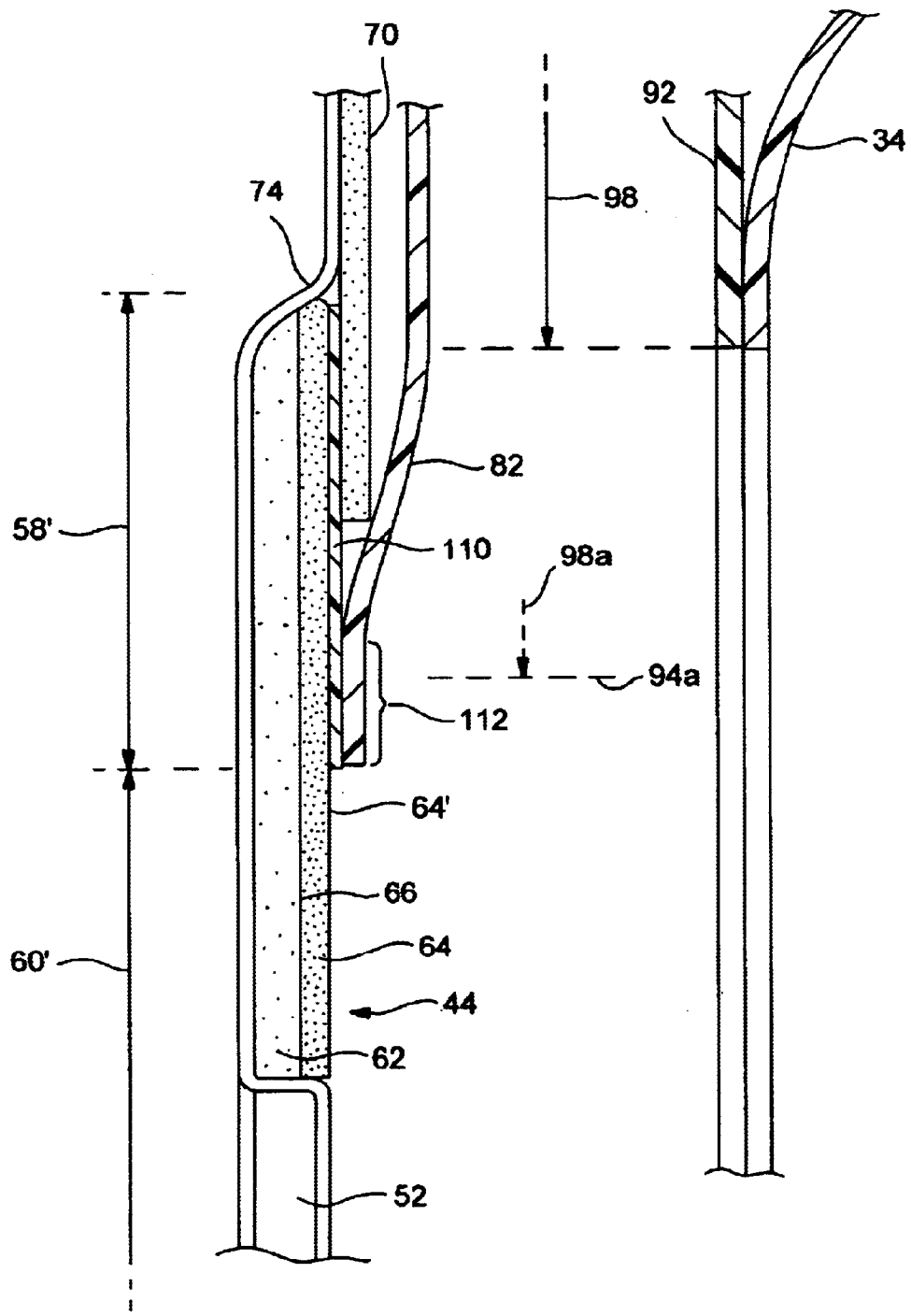
FIG. 11 is a schematic section showing a body-fitment of a fifth embodiment of the invention.

FIG. 11 shows a fifth embodiment which is similar to the fourth embodiment, except that the shape defining member 46' of the fourth embodiment is absent. Instead, a backing film 110 of a flexible plastics covers a portion of the second adhesive surface 64' of the adhesive pad 44. The backing film 110 and the adhesive pad 44 together define a first zone 60' in which the second adhesive surface 64' is exposed, and a second zone 58' in which the second adhesive surface is non-exposed. In the first zone 60', the exposed second adhesive surface 64' facilitates pliable reshaping of the pad aperture 52 (as in the previous embodiments). In the second zone 58', the backing film 110 permits the adhesive pad 44 to flex, but the backing film 110 causes the shape of the adhesive pad 44 to be more constrained in the second zone 58' than in the first zone 60'. The backing film 110 also prevents the adhesive being substantially reshaped, and prevents the second adhesive surface 64' being adhered to itself in the second zone 60'.

The adhesive pad 44 may comprise the same first and second adhesive layers 62 and 64, and the flexible sheet 66, as described in the previous embodiments.

The flange 82 is secured to the backing film 110 at a position 112 near an inner periphery of the backing film 110, for example by adhesive or by plastics welding. In the embodiment illustrated in FIG. 11, the landing zone 98 on the flange 82 is radially outside the position 112 of the join between the backing film 110 and the flange 98. However, as in the other embodiments, the landing zone may overlap the position 112 of the joint (as indicated in phantom at 98').

Although the above embodiments illustrate a microporous adhesive patch 70 surrounding the adhesive pad 44, it will be appreciated that, in other embodiments, the patch 70 may be replaced by a mass of adhesive. For example, one or more layers 62, 64 and 66, of the adhesive pad 44 may be extended radially outwardly to provide a larger adhesive surface facing towards the ostomate's body. Alternatively, a distinct layer of a skin adhesive may be used to back the adhesive pad 44, and to extend the adhesive surface radially outwardly of the pad. The skin adhesive may, for example, be the same as that used for the adhesive pad 44.

One aspect of the invention, particularly as illustrated in all of the preferred embodiments, enables an integral pad to be used to provide both a first zone in which the pad may be pliably reshaped, and a second zone having a more constrained shape.

One aspect of the invention provides that a surface of the adhesive pad facing away from the body (i.e. the second adhesive surface) includes an exposed region in the first zone, and a substantially non-exposed region in the second zone. The exposed surface in the first zone permits an aperture in the first zone to be reshaped or enlarged by rolling or folding back a rim of the adhesive surrounding the aperture into adhesive contact with a portion of the exposed adhesive surface.

Another aspect of the invention, particularly as illustrated in all of the preferred embodiments, provides an adhesive pad at least a portion of which is pliably reshapeable in a region surrounding a stomal aperture, to permit the aperture to be enlarge or reshaped. The reshapeable region comprises a laminate of a first adhesive layer, a second adhesive layer and a flexible sheet between the adhesive layers.

Another aspect of the invention enables a pliable adhesive pad to be used to provide both a fixed shape zone having a well defined shape, and a reshapeable zone in which a portion of the adhesive pad can be manually reshaped to fit an individual's stoma. The adhesive pad can be of uniform thickness and consistency in both zones, avoiding the need to provide different adhesive masses, consistencies or thicknesses to define two different zone characteristics. Also, this aspect allows a pressure applying member to be used with a shapeable adhesive.

Another aspect of the invention, particularly as illustrated in the first embodiment, enables a one-piece pouch to be provided using a shapeable adhesive providing a user-shapeable stomal aperture which can be manually reshaped from the body-facing side.

Another aspect of the invention, particularly as illustrated in the second and fourth embodiments, provides an advantageous geometry for utilizing one or more flexible flanges with a shape defining member or with a pressure applying member for applying pressure to the skin to protrude a recessed stoma. The geometry can reduce the exposure of the member to external forces.

It will be appreciated that many modifications and alternatives may be used without departing from the principles of the invention. Accordingly, the appended claims are intended to be broadly construed to include all such modifications and alternatives.

What is claimed is:

1. An ostomy body fitment for attaching an ostomy pouch to a person's body, the body fitment comprising an adhesive pad having a stomal aperture therein, at least a region of the pad immediately adjacent to the aperture being shapeable to permit the aperture to be enlarged by manually reshaping said region to fit an individual's stoma, wherein at least said shapeable region of the pad immediately adjacent to the aperture comprises a laminate of a first adhesive layer, a second adhesive layer, and a flexible sheet between said first and second adhesive layers, and said flexible sheet provides the shapeable region of the adhesive pad with a degree of memory to cause the shapeable region to at least partly tighten around a stoma after the shapeable region has been manually shaped to enlarge the stomal aperture.

2. An ostomy body fitment according to claim 1, wherein the first adhesive layer provides a first adhesive surface for contacting the person's body, the second adhesive layer provides a second adhesive surface on an opposite face of the pad to the first adhesive surface, and at least a portion of the second adhesive surface is exposed at least in use.

3. An ostomy body fitment according to claim 2, wherein the wherein the exposed second adhesive surface permits the stomal aperture to be enlarged by rolling or folding back a rim portion of the adhesive pad surrounding the aperture, into adhesive contact with a portion of the exposed second adhesive surface of the adhesive pad.

4. An ostomy body fitment according to claim 1, wherein the first adhesive layer, the second adhesive layer and the flexible sheet are substantially coextensive.

5. An ostomy body fitment according to claim 1, wherein the flexible sheet is resilient.

6. An ostomy body fitment according to claim 1, wherein the pad comprises a first shapeable zone surrounding the aperture, and a second zone having a more constrained shape surrounding the first zone.

7. An ostomy body fitment according to claim 6, wherein said adhesive pad has a substantially uniform thickness in said first and second zones.

8. An ostomy body fitment according to claim 6, wherein a thickness of the adhesive pad is substantially the same in the first zone as in the second zone.

9. An ostomy body fitment according to claim 6, wherein said adhesive pad has a substantially uniform consistency in the first and second zones.

10. An ostomy body fitment according to claim 6, wherein a consistency of the adhesive pad is substantially the same in the first zone as in the and second zone.

11. An ostomy body fitment for attaching an ostomy appliance to a person's body, the body fitment comprising:
    a pliable adhesive pad; and
    a shape defining member on one side of the adhesive pad, the shape defining member having a contour to impart a shape to the pad to cause the pad to bulge away from said one side on which the shape defining member is located, the shape defining member comprising a first aperture over which the adhesive pad at least partly extends, the pad also having a second aperture, the second aperture being smaller than, and surrounded by, the first aperture, and wherein the pad and the shape defining member together define:
- a first re-shapeable zone in which the adhesive pad is unsupported by the shape defining member, and is pliably reshapeable to enable a portion of the pad to be reshaped manually to fit an individual's stoma; and
- a second fixed-shape zone in which the adhesive pad is supported by, and has a shape defined by, the shape defining member;

wherein the portions of the pad in the first and second zones are integral with each other.

12. An ostomy body fitment according to claim 11, wherein the first re-shapeable zone is located at the first aperture of the shape defining member, and the second fixed-shape zone surrounds the first zone.

13. An ostomy body fitment according to claim 11, wherein the adhesive pad has a substantially uniform thickness in the first and second zones.

14. An ostomy body fitment according to claim 11, wherein the adhesive pad has substantially the same thickness in the first and second zones.

15. An ostomy body fitment according to claim 11, wherein the pad has a substantially uniform consistency in the first and second zones.

16. An ostomy body fitment according to claim 11, wherein a linear dimension of the second aperture is not more than two thirds of a corresponding linear dimension of the first aperture.

17. An ostomy body fitment according to claim 16, wherein said linear dimension of the second aperture is not more than a half of said linear dimension of the first aperture.

18. An ostomy body fitment according to claim 11, wherein a width of the first zone from an edge of the first aperture to a closest edge of the second aperture is at least 3 mm.

19. An ostomy body fitment according to claim 18, wherein said width from the first zone from said edge of the first aperture to said closest edge of the second aperture is at least 5 mm.

20. An ostomy body fitment according to claim 11, wherein said adhesive pad comprises a laminate of a first adhesive layer, a second adhesive layer, and a flexible sheet between the first and second adhesive layers.

21. An ostomy body fitment according to claim 11, further comprising a coupling portion for enabling the body fitment to be releasably coupled to said ostomy appliance.

22. An ostomy body fitment according to claim 11, wherein said body fitment is permanently attached to an ostomy pouch.

* * * * *